United States Patent
Nagashima et al.

(10) Patent No.: US 7,919,154 B2
(45) Date of Patent: Apr. 5, 2011

(54) 1-(TRIFLUOROMETHYL)NAPHTHALENE DERIVATIVE

(75) Inventors: Yutaka Nagashima, Kitaadachi-gun (JP); Tetsuo Kusumoto, Kitaadachi-gun (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 12/449,896

(22) PCT Filed: Mar. 3, 2008

(86) PCT No.: PCT/JP2008/053765
§ 371 (c)(1),
(2), (4) Date: Sep. 2, 2009

(87) PCT Pub. No.: WO2008/111417
PCT Pub. Date: Sep. 18, 2008

(65) Prior Publication Data
US 2010/0140547 A1   Jun. 10, 2010

(30) Foreign Application Priority Data

Mar. 9, 2007  (JP) ................................. 2007-059945

(51) Int. Cl.
*C09K 19/32* (2006.01)
*C09K 19/30* (2006.01)
*C07C 43/225* (2006.01)
*C07C 25/18* (2006.01)

(52) U.S. Cl. ................ 428/1.1; 252/299.61; 252/299.62; 568/634; 570/183; 570/187

(58) Field of Classification Search .................... 428/1.1; 252/299.61, 299.62, 299.63; 570/183, 187; 568/634

See application file for complete search history.

(56) References Cited

U.S. PATENT DOCUMENTS

| 4,386,007 A | * | 5/1983 | Krause et al. | ............ 252/299.62 |
| 7,662,442 B2 | * | 2/2010 | Nagashima | ..................... 428/1.1 |
| 7,803,435 B2 | * | 9/2010 | Takeshita et al. | .............. 428/1.1 |

FOREIGN PATENT DOCUMENTS

| DE | 19522195 A1 | 12/1995 |
| JP | 02-503441 T | 10/1990 |
| JP | 08-040953 A | 2/1996 |
| JP | 10-176167 A | 6/1998 |
| JP | 2000-109843 A | 4/2000 |
| JP | 2000-119653 A | 4/2000 |
| JP | 2008-222588 A | 9/2008 |
| WO | WO-89/08633 A1 | 9/1989 |

OTHER PUBLICATIONS

Office Action drafted Sep. 26, 2008, issued on the corresponding Japanese application No. 2008-513850 and the brief English translation thereof.
International Search Report mailed May 13, 2008, issued on PCT/JP2008/053765.

* cited by examiner

*Primary Examiner* — Shean C Wu
(74) *Attorney, Agent, or Firm* — Edwards Angell Palmer & Dodge LLP

(57) ABSTRACT

Since a 1-(trifluoromethyl)naphthalene derivative of the present invention has negative dielectric anisotropy, has a very large absolute value, is chemically stable with heat, light, water, and the like, moreover, it excels in compatibility with a liquid crystal compound or a liquid crystal composition used widely nowadays, it is suitable as an element of a practical liquid crystal composition capable of low voltage drive. In addition, the liquid crystal composition using the compound of the present invention has low drive voltage, is useful as a constituent material of the liquid crystal display device of low consumption of electrical power, and can be used suitably for liquid crystal display devices such as a VA type and an IPS type, and the like.

20 Claims, No Drawings

1-(TRIFLUOROMETHYL)NAPHTHALENE DERIVATIVE

TECHNICAL FIELD

The present invention relates to a new liquid crystalline compound which has 1-(trifluoromethyl)naphthyl group useful as an electrooptic liquid crystal display material, a liquid crystal composition containing thereof, and a liquid crystal display device using it.

BACKGROUND ART

A liquid crystal display device is widely used now because of excellent features of low voltage operation and thin type display, and the like. A TN (Twisted Nematic), a STN (Super-Twisted Nematic), or an active matrix (TFT: thin film transistor) based on the TN, and the like are used for the display type of the conventional liquid crystal display device, which use a liquid crystal composition with a positive dielectric anisotropy value. However, narrowness of a viewing angle is one of weak points for these display types, and its improvement is a big problem with the greater demand of enlargement of a liquid crystal panel in recent years.

In order to solve this problem, display modes such as vertical alignment mode, IPS (In-Plane-Switching) and the like have newly been put into practical use in recent years. The vertical alignment mode is the mode aimed at improving the viewing angle by use of vertical orientation of liquid crystal molecules, which uses liquid crystal compositions having negative dielectric anisotropy ($\Delta\in$). On the other hand, IPS is the method aimed at improving the viewing angle by switching the liquid crystal molecules using horizontal lateral electric field against a glass substrate, which liquid crystal composition having positive $\Delta\in$ or negative $\Delta\in$ is used. Thus, the liquid crystal compound and liquid crystal composition having negative $\Delta\in$ are necessary as the vertical alignment mode and the IPS for the effective display modes which improve the viewing angle, and they have been desired strongly. Formerly, compounds having 2,3-difluorophenylene group have been mainly used as the composition having negative $\Delta\in$ (as refer to patent document 1). However, a problem exists that the absolute value of $\Delta\in$ of the liquid crystal composition using the compound is not sufficiently large (as refer to patent document 2).

Therefore, a trifluoronaphthalene derivative is reported as a compound having negative $\Delta\in$ of a larger absolute value than the compound having 2,3-difluorophenylene group (as refer to patent document 3). However, the demand for further reducing the consumption of electric power in a liquid crystal display device is strong, and, in this issue, the absolute value of $\Delta\in$ is not sufficiently large even in case of using a trifluoronaphthalene moiety.

On the other hand, a compound having a trifluoromethyl group at a lateral position of benzene ring (as refer to patent document 4) is reported. Furthermore, it is also reported that the compound described in the cited document can be advantageously used as an element of the liquid crystal composition having negative $\Delta\in$ of a larger absolute value. However, the compound having a trifluoromethyl group at a lateral position of benzene ring has a problem that the absolute value of dielectric anisotropy does not attain sufficiently large because of the following reason. That is, in the compound having negative $\Delta\in$, in order to make the absolute value of $\Delta\in$ larger, it is necessary to replace substituent groups having large electron-withdrawing group at a lateral position of benzene. However, since a 1,4-phenylene group has only two lateral substituent positions as 2-substituted position and 3-substituted position, a limit to increase the absolute value of $\Delta\in$ exists.

Moreover, in the structure such as a biphenyl moiety which is connected with two 1,4-phenylene groups, the electron-withdrawing group replaced on two adjacency phenylene groups hardly turns to the same direction, and the absolute value of $\Delta\in$ does not generally increase.

Thus, as mentioned above, development of the compound having an absolute value of larger $\Delta\in$ in a negative $\Delta\in$ compound has been desired.

Patent document 1: JP-T-H02-503441
Patent document 2: JP-A-H10-176167
Patent document 3: DE: 195 22 195 Description
Patent document 4: JP-A-H08-40953

DISCLOSURE OF INVENTION

Problems to be Solved

The problems to be solved in the present invention relates to provide a compound having larger absolute value of $\Delta\in$ in a negative $\Delta\in$ compound, and to provide a practical liquid crystal composition by using the compound thereof.

SUMMARY OF THE INVENTION

The present invention provides a 1-(trifluoromethyl)naphthalene derivative represented by the general formula (I) as a means for solving the above-mentioned problems, provides a liquid crystal composition containing one or more kinds of compounds represented by the general formula (I), and further provides a liquid crystal device in which a component is the liquid crystal composition.

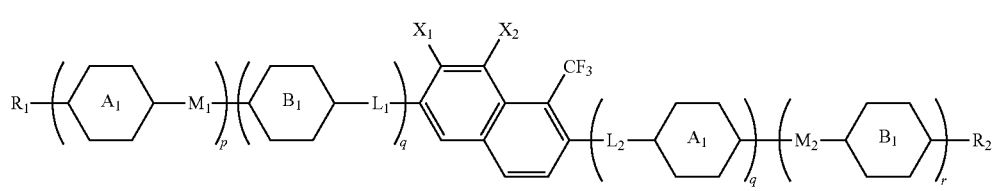

(I)

(In the formula, each $R_1$ and $R_2$ represents independently an alkyl group having 1 to 12 carbon numbers, an alkenyl group having 2 to 12 carbon numbers, an alkoxyl group having 1 to 12 carbon numbers, or an alkenyloxy group having 2 to 12 carbon numbers;

each one or more hydrogen atoms may be independently replaced with a fluorine atom, and each —$CH_2$— group may be independently replaced with —O—, —S—, —CO—, —COO—, —OCO—, or —OCOO—;

each $A_1$, $A_2$, $B_1$, and $B_2$ represents independently a trans-1,4-cyclohexylene group, a trans-1,3-dioxane-2,5-diyl group, a pyridine-2,5-diyl group, a pyrimidine 2,5-diyl group, or a 1,4-phenylene group which may be replaced with one or more fluorine atoms;

each $L_1$, $L_2$, $M_1$, and $M_2$ represents independently a single bond, —$CH_2CH_2$—, —CH═CH—, —CH≡CH—, —$OCH_2$—, —$CH_2O$—, —$OCF_2$—, —$CF_2O$—, —$CF_2CF_2$—, —CF═CF—, —OCO—, —COO—, —$CH(CH_3)CH_2$—, —$CH_2CH(CH_3)$—, —$CH(CH_3)CH(CH_3)$—, —$OCH(CH_3)$—, —$CH(CH_3)O$—, —$(CH_2)_4$—, —$(CH_2)_3O$—, —$O(CH_2)_3$—, —COS—, or —SCO—;

each $X_1$ and $X_2$ represents independently a hydrogen atom or a fluorine atom; and each p, q, r, and s represents independently 0 or 1.)

A liquid crystal compound of the present invention is characterized in that a trifluoromethyl group having very large electron-withdrawability is replaced at 1-substituted position of a naphthalene ring. Therefore, a liquid crystal compound having this moiety has large polarization in the direction of a minor axis of a molecule, and has a negative dielectric anisotropy with a large absolute value as a result.

EFFECT OF THE INVENTION

A compound represented by the general formula (I) of the present invention has a Δ∈ of negative and extremely large absolute value. Furthermore, since it is chemically stable with heat, light, water and the like, and excels in compatibility with a liquid crystal compound or a liquid crystal composition widely used now, so it is suitable as an element of the practical liquid crystal composition in which low voltage drive is possible.

BEST MODE FOR CARRYING OUT THE INVENTION

In the general formula (I), each $R_1$ and $R_2$ represents independently an alkyl group having 1 to 12 carbon numbers, an alkenyl group having 2 to 12 carbon numbers, an alkoxyl group having 1 to 12 carbon numbers, or an alkenyloxy group having 2 to 12 carbon numbers, each one or more hydrogen atoms may be replaced independently with a fluorine atom, and each —$CH_2$— group may be replaced independently with —O—, —S—, —CO—, —COO—, —OCO—, or —OCOO—; it is preferable that each $R_1$ and $R_2$ is an alkyl group having 1 to 8 carbon numbers, an alkenyl group having 2 to 8 carbon numbers, an alkoxyl group having 1 to 7 carbon numbers, or an alkenyloxy group having 2 to 7 carbon numbers; and it is more preferable that each $R_1$ and $R_2$ is a linear alkyl group having 2 to 5 carbon atoms, a vinyl group, a 3-butenyl group, a trans-1-propene-1-yl group, or a trans-3-pentene-1-yl group.

Each $A_1$, $A_2$, $B_1$, and $B_2$ represents independently a trans-1,4-cyclohexylene group, a trans-1,3-dioxane-2,5-diyl group, a pyridine-2,5-diyl group, a pyrimidine 2,5-diyl group, or a 1,4-phenylene group which may be replaced with one or more fluorine atoms; it is preferable that each $A_1$, $A_2$, $B_1$, and $B_2$ is a trans-1,4-cyclohexylene group or a 1,4-phenylene group which may be replaced with one or more fluorine atoms; and it is more preferable that they is a trans-1,4-cyclohexylene group or a 1,4-phenylene group without substitution.

Each $L_1$, $L_2$, $M_1$, and $M_2$ represents independently a single bond, —$CH_2CH_2$—, —CH═CH—, —$OCH_2$—, —$CH_2O$—, —$OCF_2$—, —$CF_2O$—, —$CF_2CF_2$—, —CF═CF—, —OCO—, —COO—, —$CH(CH_3)CH_2$—, —$CH_2CH(CH_3)$—, —$CH(CH_3)CH(CH_3)$—, —$OCH(CH_3)$—, —$CH(CH_3)O$—, —$(CH_2)_4$—, —$(CH_2)_3O$—, —$O(CH_2)_3$—, —COS—, or —SCO—; it is preferable that each is independently a single bond, —$CH_2CH_2$—, —$OCH_2$—, —$CH_2O$—, —$OCF_2$—, —$CF_2O$—, or —$CF_2CF_2$—; and it is more preferable that each is a single bond or —$CH_2CH_2$—.

Each $X_1$ and $X_2$ represent independently a hydrogen atom or a fluorine atom, and, in order to make Δ∈ larger, it is preferable that each $X_1$ and $X_2$ is a fluorine atom. While p, q, r, and s represents 0 or 1, it is preferable that the sum of p, q, r and s is an integer of 1 or more and 3 or less, and it is more preferable that the sum of p, q, r and s is 1 or 2.

Although compounds of the general formula (I) may include various kinds of compounds as mentioned above by selection of $R_1$, $R_2$, $A_1$, $A_2$, $B_1$, $B_2$, $L_1$, $L_2$, $M_1$, $M_2$, $X_1$, $X_2$, p, q, r, and s; among these, each compound represented by the following general formula (I-a-a) to general formula (I-h-k) is preferable.

[Chemical formula 2]

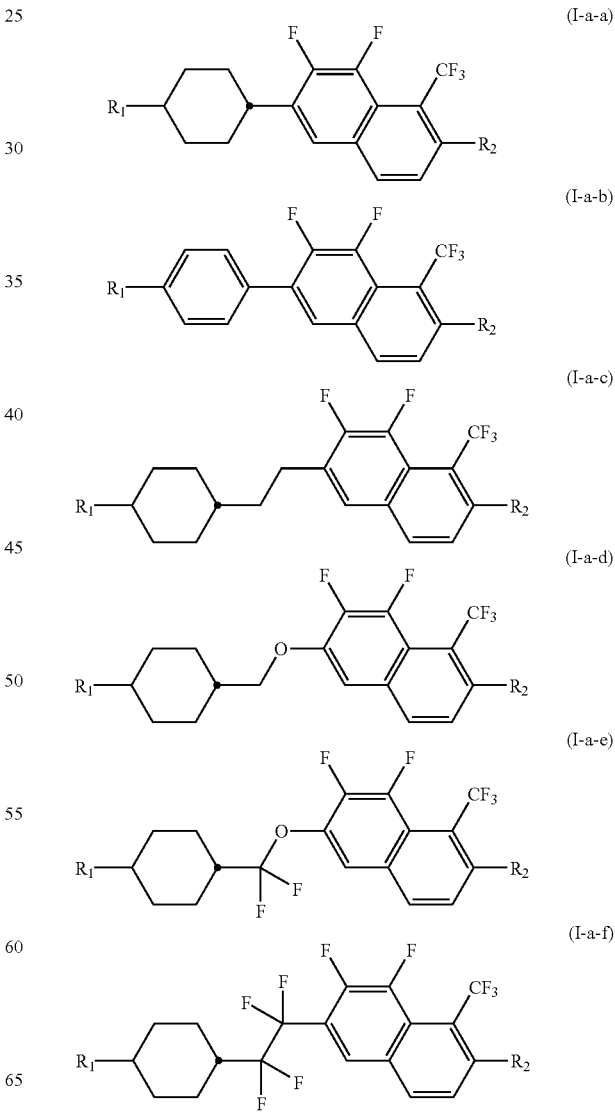

-continued
(I-a-g)
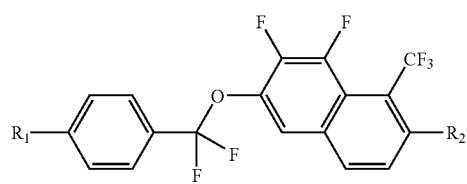
[Chemical formula 3]
(I-b-a)
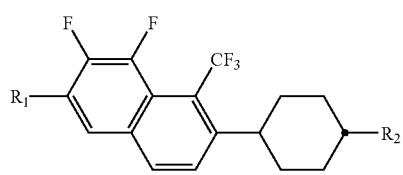
(I-b-b)
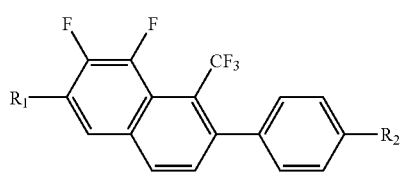
(I-b-c)
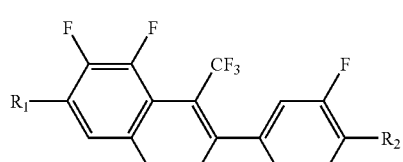
(-b-d)
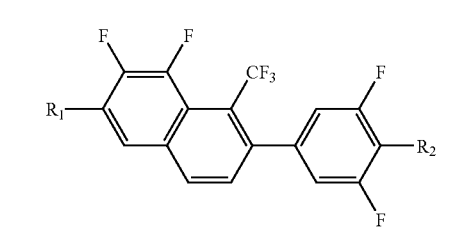
(I-b-e)
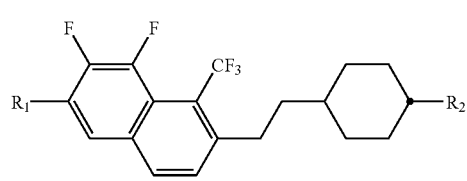
(I-b-f)
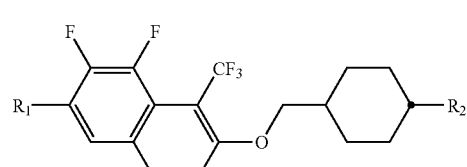
(I-b-g)
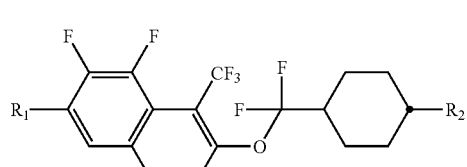
(I-b-h)
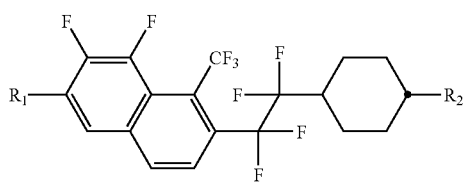
(I-b-i)
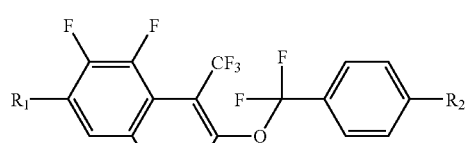
[Chemical formula 4]
(I-c-a)
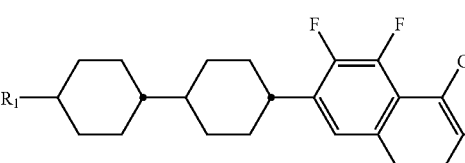
(I-c-b)
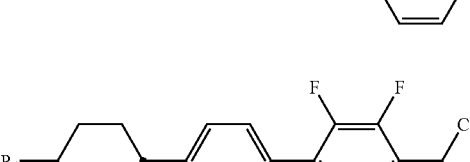
(I-c-c)
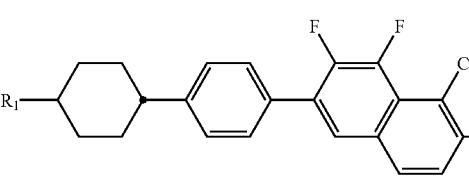
(I-c-d)
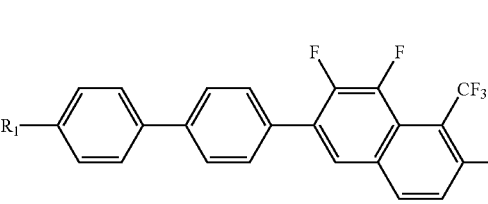
(I-c-e)
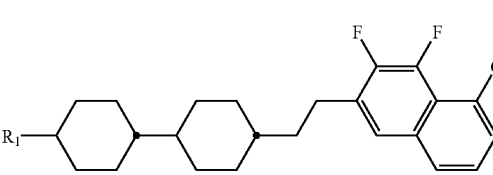
(I-c-f)
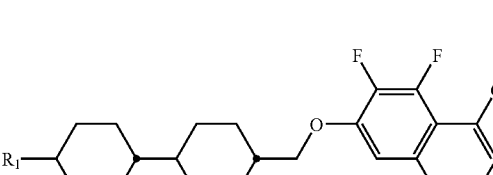

(I-c-g)
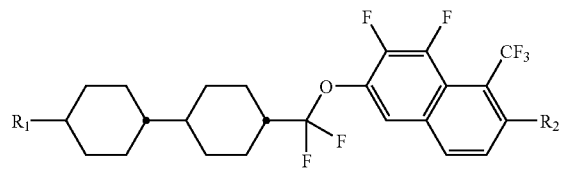
(I-c-h)
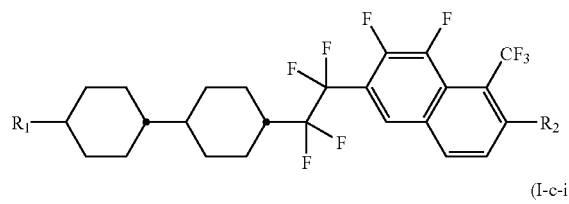
(I-c-i)
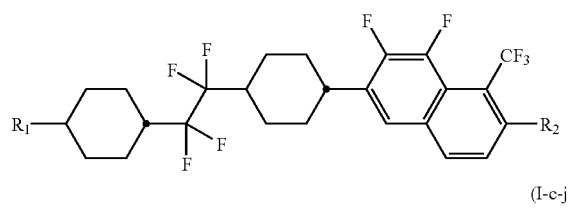
(I-c-j)
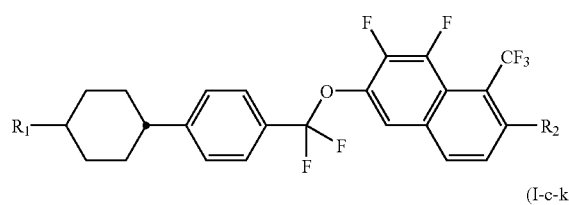
(I-c-k)
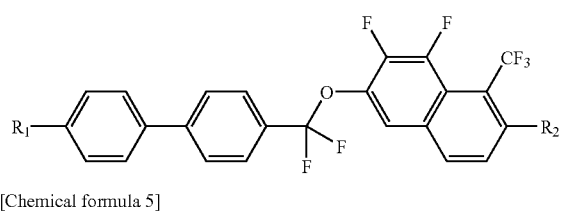
[Chemical formula 5]
(I-d-a)
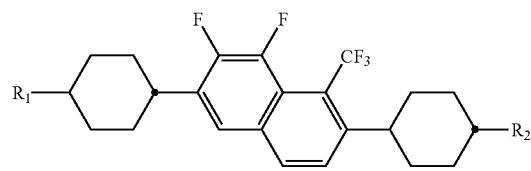
(I-d-b)
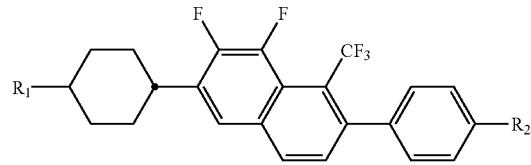
(I-d-c)
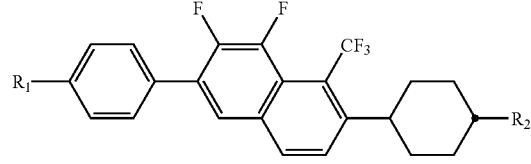
(I-d-d)
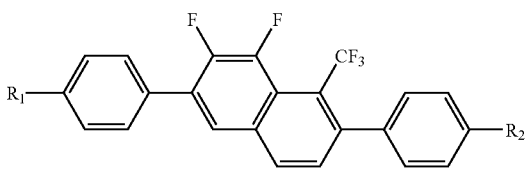
[Chemical formula 6]
(I-e-a)
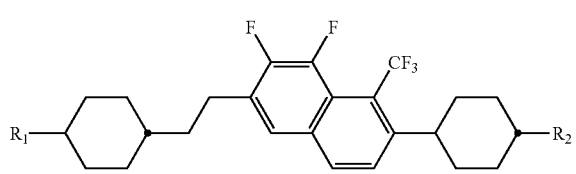
(I-e-b)
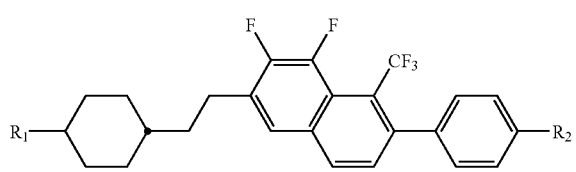
(I-e-c)
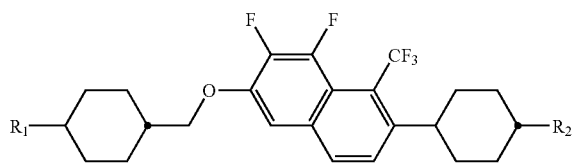
(I-e-d)
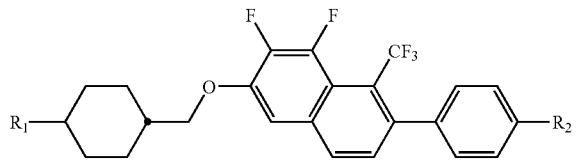
(I-e-e)
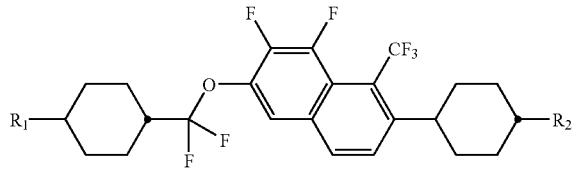
(I-e-f)
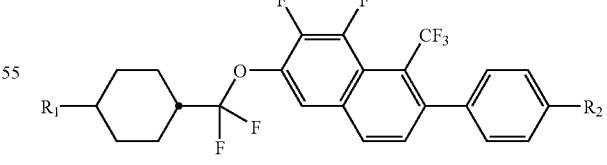
(I-e-g)
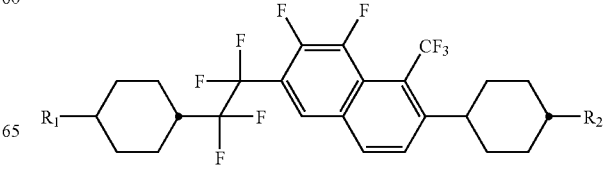

(I-e-h)
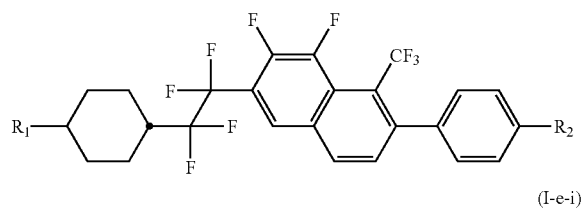
(I-e-i)
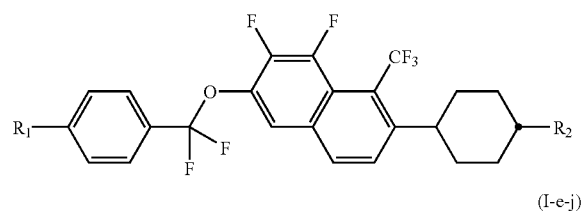
(I-e-j)
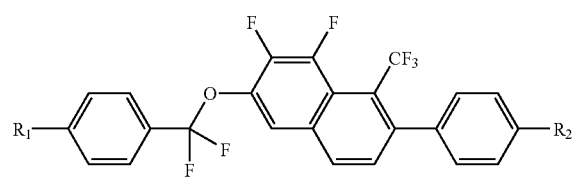
[Chemical formula 7]
(I-f-a)
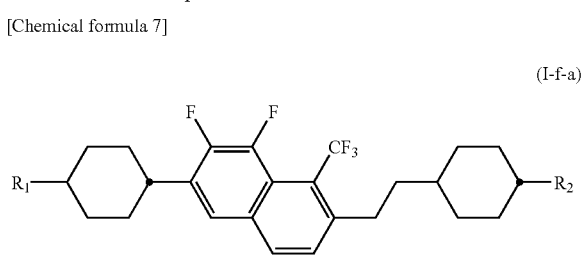
(I-f-b)
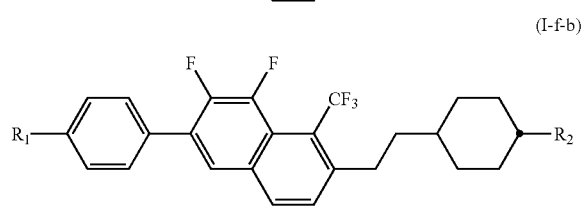
(I-f-c)
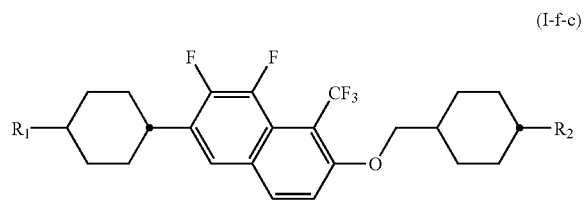
(I-f-d)
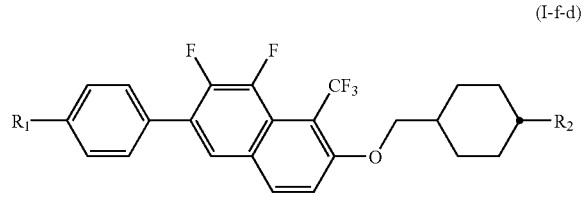
(I-f-e)
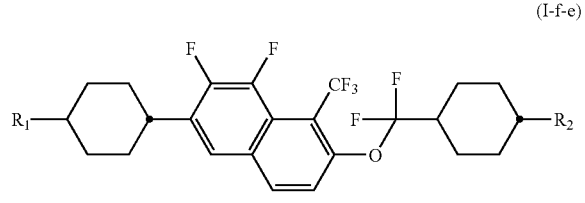
(I-f-f)
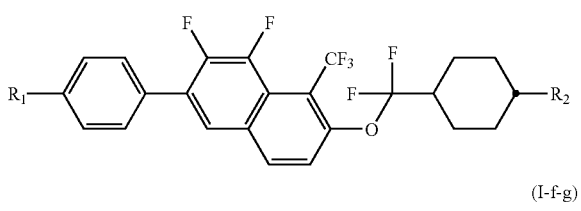
(I-f-g)
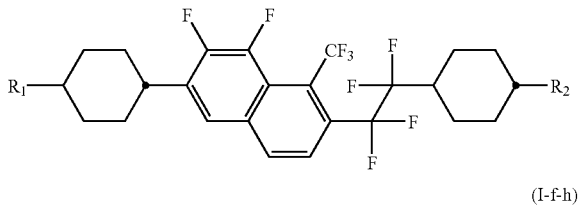
(I-f-h)
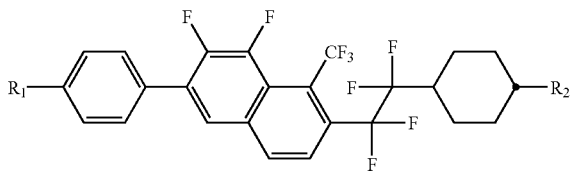
(I-f-i)
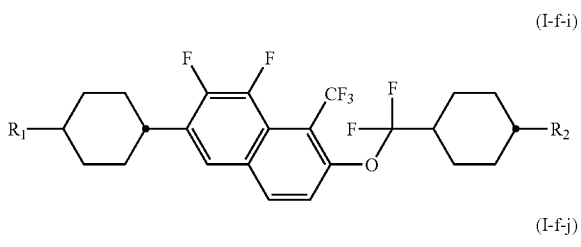
(I-f-j)
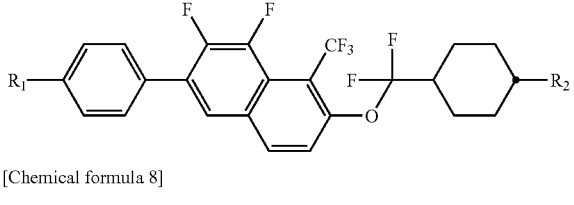
[Chemical formula 8]
(I-g-a)
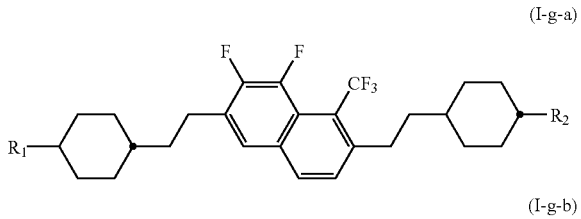
(I-g-b)
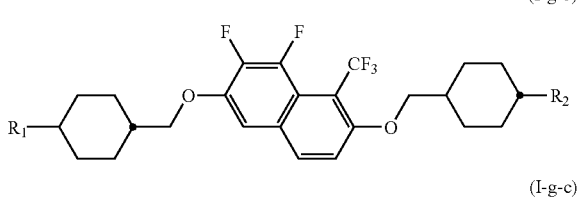
(I-g-c)
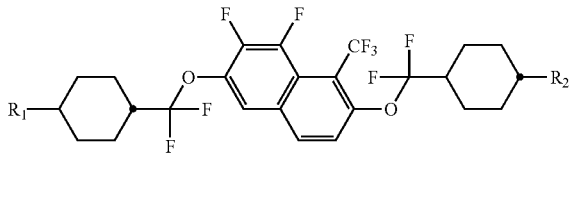

-continued (I-g-d)
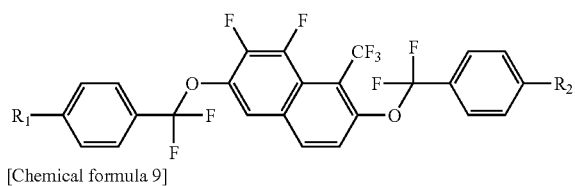

[Chemical formula 9]

(I-h-a)
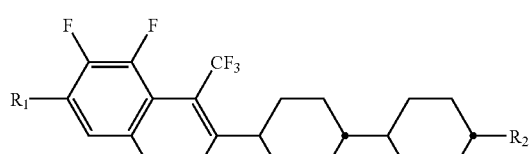

(I-h-b)
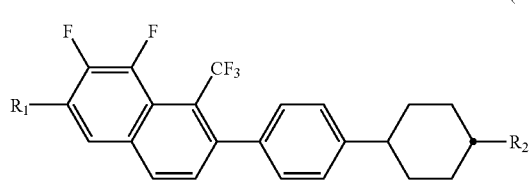

(I-h-c)
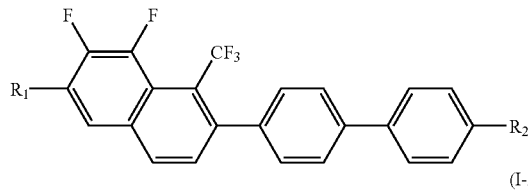

(I-h-d)
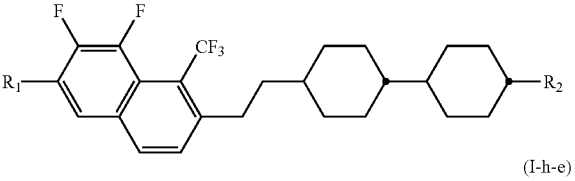

(I-h-e)
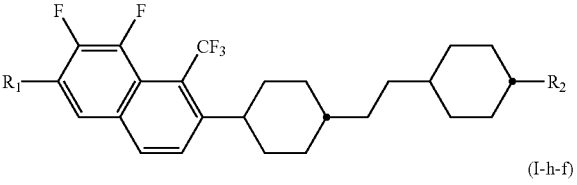

(I-h-f)
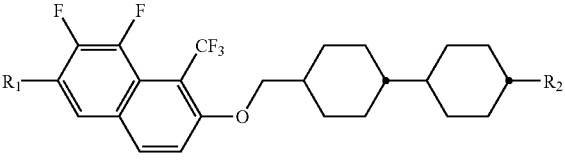

-continued (I-h-g)
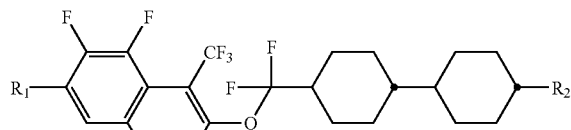

(I-h-h)

(I-h-i)

(I-h-j)

(I-h-k)

(In the formulas, each $R_1$ and $R_2$ represents an alkyl group having 1 to 8 carbon numbers, an alkenyl group having 2 to 8 carbon numbers, an alkoxyl group having 1 to 7 carbon numbers, or an alkenyloxy group having 2 to 7 carbon numbers.)

Furthermore, in the above formulas, each compound of a general formula (I-a-a) to a general formula (I-a-d), a general formula (I-b-c) to a general formula (I-b-e), a general formula (I-c-a) to a general formula (I-c-e), and a general formula (I-d-c) to a general formula (I-d-d) is particularly preferable.

A compound of (I) of the present invention can be prepared, for example, as follows.

A naphthalene derivative represented by the general formula (II)

[Chemical formula 10]

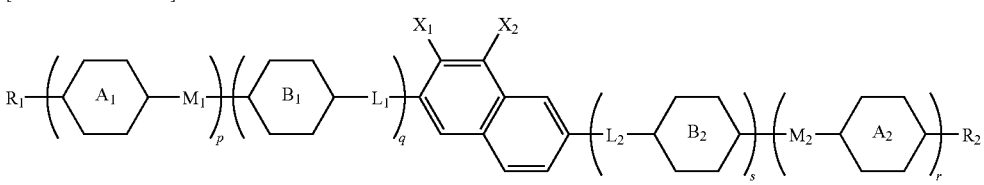

(II)

(In the formula, $R_1$, $R_2$, $A_1$, $A_2$, $B_1$, $B_2$, $L_1$, $L_2$, $M_1$, $M_2$, $X_1$, $X_2$, p, g, r, and s represent the same meaning with the general formula (I).) is iodized with N-iodosuccinimide, iodine, and the like; and a 1-iodonaphthalene derivative (III) is obtained.

[Chemical formula 11]

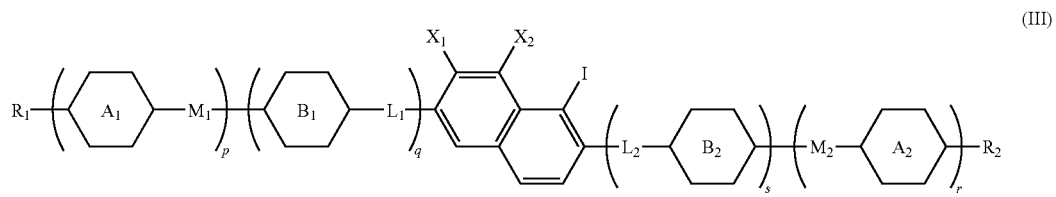

(III)

(In the formula, $R_1$, $R_2$, $A_1$, $A_2$, $B_1$, $B_2$, $L_1$, $L_2$, $M_1$, $M_2$, $X_1$, $X_2$, p, q, r, and s represent the same meaning with the general formula (I).) The compound represented by the general formula (I) can be obtained by acting trifluoromethyltrimethylsilane on the obtained compound (III) in the presence of a fluorinated compound such as sodium fluoride, potassium fluoride, cesium fluoride, and the like and a copper salt such as copper(I) chloride, copper(I) bromide, copper(I) iodide, and the like in a nonpolar protic solvent such as N,N-dimethylformamide, N-methylpyrrolidone, dimethyl sulfoxide, and the like.

Or a 1-iodo-2-naphthol derivative (V) is obtained by acting N-iodosuccinimide, iodine, and the like on a 2-naphthol derivative (IV).

[Chemical formula 12]

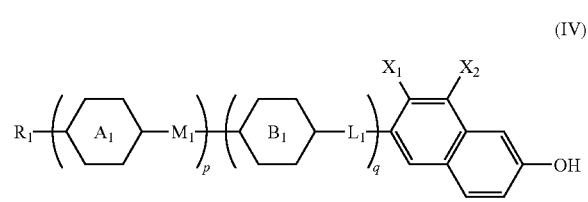

(IV)

(In the formula, $R_1$, $A_1$, $B_1$, $L_1$, $M_1$, $X_1$, $X_2$, p and q represent the same meaning with the general formula (I).)

[Chemical formula 13]

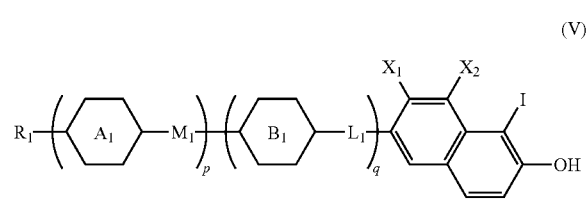

(V)

(In the formula, $R_1$, $A_1$, $B_1$, $L_1$, $M_1$, $X_1$, $X_2$, p and q represent the same meaning with the general formula (I).) A 1-iodo naphthalene derivative (VI) is obtained by acting trifluoromethanesulfonic anhydride, p-toluensulfonyl chloride, methanesulfonyl chloride, and the like on the obtained 1-iodo-2-naphthol derivative (V) in the presence of a base such as pyridine and triethylamine, and the like.

[Chemical formula 14]

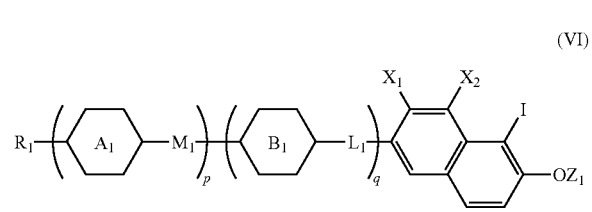

(VI)

(In the formula, $R_1$, $A_1$, $B_1$, $L_1$, $M_1$, $X_1$, $X_2$, p and q represent the same meaning with the general formula (I), and $Z_1$ represents a leaving group such as a trifluoromethanesulfonyl group, a p-toluenesulfonyl group, a methanesulfonyl group, and the like.)

A compound represented by the general formula (III) can also be obtained by acting an organometallic compound (VII) on the compound (VI) in the presence of a transition metal catalyst of a palladium system, a nickel system, or an iron system such as tetrakis(triphenylphosphine)palladium(0), (1,2-bis(diphenylphosphino)ethane)dichloronickel(II), tris(acetylacetonato)iron (III), and the like.

[Chemical formula 15]

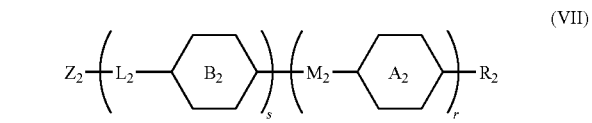

(VII)

(In the formula, $R_2$, $A_2$, $B_2$, $L_2$, $M_2$, r and s represent the same meaning with the general formula (I), and $Z_2$ represents a metal or a metallic salt such as magnesium chloride, zinc chloride, lithium, copper, copper-lithium, trialkylsilane, boric acid, and the like.)

Or, a naphthalene derivative (VIII) is obtained by acting trifluoromethanesulfonic anhydride, p-toluensulfonyl chloride, methanesulfonyl chloride, and the like on the 2-naphthol derivative (IV) in the presence of a base such as pyridine, triethylamine, and the like.

[Chemical formula 16]

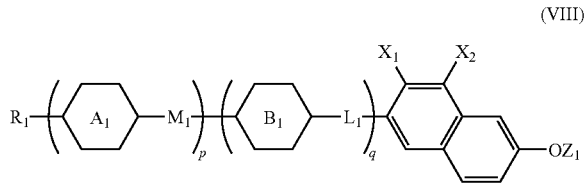

(VIII)

(In the formula, $R_1$, $A_1$, $B_1$, $L_1$, $M_1$, $X_1$, $X_2$, p and q represent the same meaning with the general formula (I), and $Z_1$ represents a leaving group such as a trifluoromethanesulfonyl group, a p-toluenesulfonyl group, a methanesulfonyl group, and the like.) A 1-iodo naphthalene derivative (VI) can also be obtained by acting N-iodosuccinimide, iodine, and the like on the obtained compound (VIII).

Or, a 1-(trifluoromethyl)-2-naphthol derivative (IX) is obtained by acting trifluoromethyltrimethylsilane on the 1-iodo-2-naphthol derivative (V), in the presence of a fluorinated compound such as sodium fluoride, potassium fluoride, cesium fluoride, and the like and a copper salt such as copper (I) chloride, a copper(I) bromide, a copper(I) iodide, and the like in a nonpolar protic solvent such as N,N-dimethylformamide, N-methylpyrrolidone, dimethyl sulfoxide, and the like.

[Chemical formula 17]

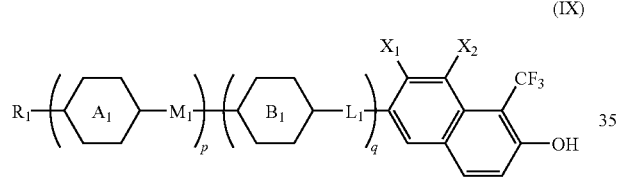

(IX)

(In the formula, $R_1$, $A_1$, $B_1$, $L_1$, $M_1$, $X_1$, $X_2$, p and q represent the same meaning with the general formula (I).)

A 1-(trifluoromethyl)naphthalene derivative (X) is obtained by acting trifluoromethanesulfonic anhydride, p-toluensulfonyl chloride, methanesulfonyl chloride, and the like on the obtained 1-(trifluoromethyl)-2-naphthol derivative (IX), in the presence of a base such as pyridine, triethylamine, and the like.

[Chemical formula 18]

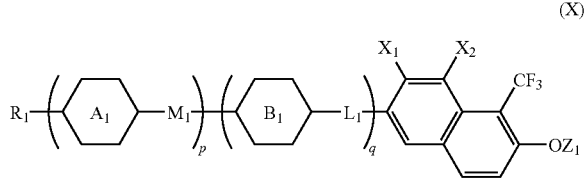

(X)

(In the formula, $R_1$, $A_1$, $B_1$, $L_1$, $M_1$, $X_1$, $X_2$, p and q represent the same meaning with the general formula (I), and $Z_1$ represents a leaving group such as a trifluoromethanesulfonyl group, a p-toluenesulfonyl group, a methanesulfonyl group, and the like.)

A compound represented by the general formula (I) can also be obtained by acting an organometallic compound (VII) on the obtained compound (X) in the presence of transition metal catalyst of palladium, nickel, or iron such as tetrakis(triphenylphosphine)palladium(0), (1,2-bis(diphenylphosphino)ethane)dichloronickel(II), tris(acetylacetonato)iron(III) and the like.

Many of the compounds represented by the general formula (I) show comparatively excellent compatibility to other liquid crystal materials. Moreover, they can also obtain easily high resistivity and high voltage holding ratio. Therefore, they can be used suitably as a material for liquid crystal display cell in the state of a mixture with other liquid crystal compounds. A compound represented by the general formula (I) can increase the absolute value of Δ∈ greatly by adding it, can reduce the threshold voltage, also has an advantage of possibility of both of a high-speed response and an increase in birefringence (Δn). Therefore, the compounds represented by the general formula (I) can be used in any of the various above-mentioned display types. Besides, it is suitable to be used for a TN type display device of a simple matrix drive or of an active-matrix drive, and for a STN display device; and it is preferable to be used particularly as a polar element for the liquid crystal material of a TN display device of an active-matrix drive.

Thus, as a preferable representative example of the nematic liquid crystal compound which can be used by mixing with the compound represented by the general formula (I), in the compositions provided by the present invention, it is preferable to contain at least one kind of the compound represented by the general formula (I) as the first element, and contains one or more kinds of compounds represented particularly by the following general formula (A) as other elements.

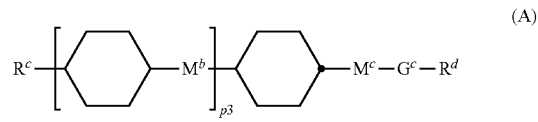

(A)

(In the formula, $R^c$ represents a linear alkyl group or an alkenyl group having 1 to 7 carbon atoms, $R^d$ represents a linear alkyl group, an alkenyl group, an alkoxyl group, or an alkenyloxy group having 1 to 12 carbon atoms, p3 represents 0 or 1, each $M^b$ and $M^c$ represent independently a single bond, —COO—, or —CH$_2$CH$_2$—, and $G^c$ represents a trans-1,4-cyclohexylene group or a -1,4-phenylene group.)

In the general formula (A), it is preferable that $R^c$ is a linear alkyl group having 2 to 7 carbon atoms, a 1-alkenyl group having 2 to 5 carbon atoms, or a 3-alkenyl group having 4 to 5 carbon atoms; as a linear alkyl group, an ethyl group, a propyl group, a butyl group, or a pentyl group is more preferable; as a 1-alkenyl group, a vinyl group or a trans-1-propenyl group is more preferable; and as a 3-alkenyl group, a 3-butenyl group or a trans-3-pentenyl group is more preferable. It is preferable that $R^d$ is a linear alkyl group having 1 to 7 carbon atoms, a 1-alkenyl group having 2 to 5 carbon atoms, a 3-alkenyl group having 4 to 5 carbon atoms, and a linear alkoxyl group having 1 to 3 carbon atoms. In the case when $M^b$ exists, it is preferable that at least one part of $M^b$ and $M^c$ is a single bond.

As a compound represented by the general formula (A), a compound represented by the following general formula (A-1) to the following general formula (A-14) is preferable, and a compound represented by the general formula (A-1), the general formula (A-2), the general formula (A-3), the general formula (A-5), or the general formula (A-6) is particularly preferable.

[Chemical formula 20]

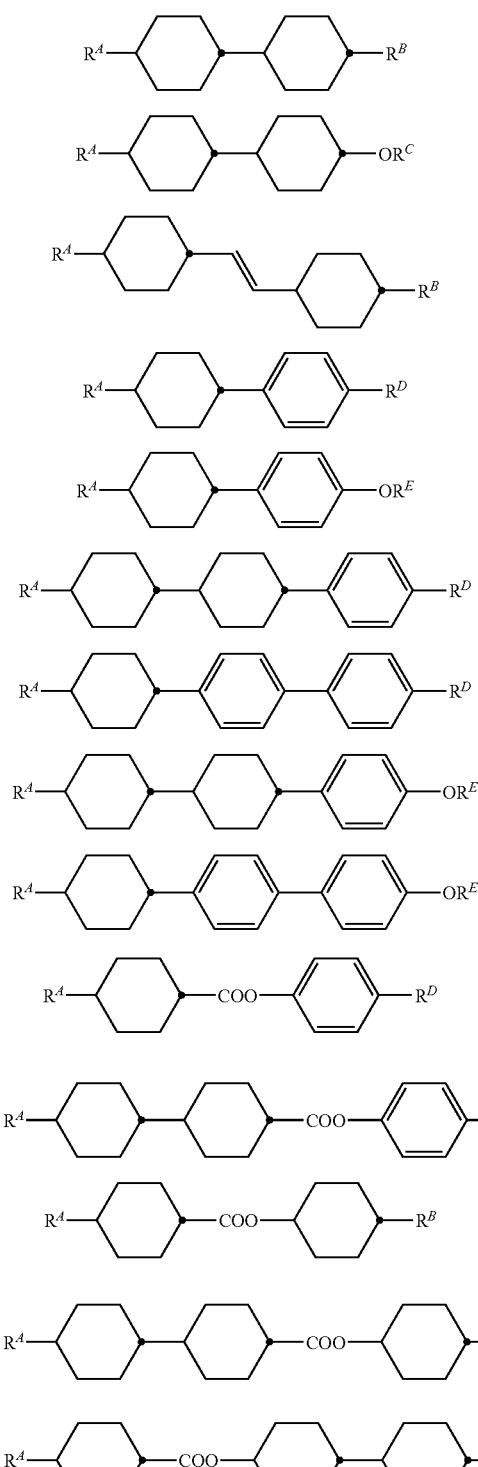

(In the formula, each $R^A$ and $R^B$ represents independently a linear alkyl group having 1 to 7 carbon atoms, a 1-alkenyl group having 2 to 3 carbon atoms, or a 3-alkenyl group having 4 to 5 carbon atoms; $R^C$ represents a linear alkyl group having 1 to 5 carbon atoms, or a linear 2-alkenyl group having 3 to 4 carbon atoms; $R^D$ represents a linear alkyl group having 1 to 3 carbon atoms, or a 3-alkenyl group having 4 to 5 carbon atoms; and $R^E$ represents a linear alkyl group having 1 to 3 carbon atoms, or a linear 2-alkenyl group having 3 to 4 carbon atoms.)

In the liquid crystal composition of the present invention,

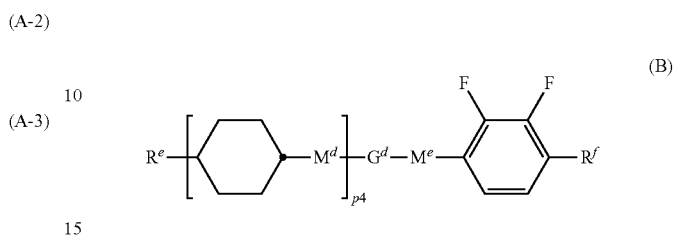

(In the formula, $R^e$ represents an alkyl group having 1 to 7 carbon atoms; $R^f$ represents a linear alkyl group, an alkoxyl group, or an alkenyloxy group having 1 to 7 carbon atoms; p4 represents 0 or 1; each $M^d$ and $M^e$ represent independently a single bond, —CH$_2$CH$_2$—, —OCH$_2$—, —CH$_2$O—, —OCF$_2$—, —CF$_2$O—, or —COO—; and $G^d$ represents a trans-1,4-cyclohexylene group or an -1,4-phenylene group which may be replaced with 1 or 2 fluorine atoms.) one or more kinds of 2,3-difluoro-1,4-phenylene derivatives represented by the general formula (B) may be contained.

In the general formula (B), it is preferable that $R^e$ is a linear alkyl group having 2 to 7 carbon atoms. It is preferable that $R^f$ is a linear alkyl group and a linear alkoxyl group having 1 to 5 carbon atoms; and a linear alkyl group having 1 to 4 carbon atoms, or a linear alkoxyl group having 1 to 4 carbon atoms is particularly preferable. It is preferable that one of $M^d$ and $M^e$ is a single bond, and that the other is a single bond, —CH$_2$CH$_2$— or —COO—.

Although a great many compounds are included in the general formula (B), compounds represented by the following general formula (B-1) to the general (B-9) are preferable.

[Chemical formula 22]

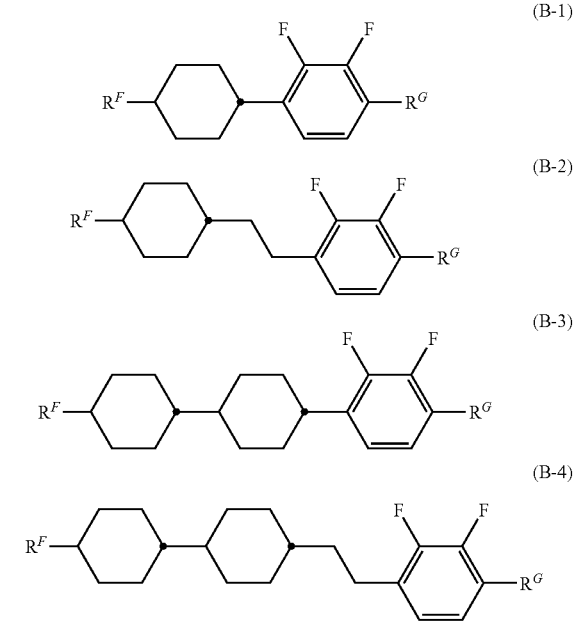

-continued

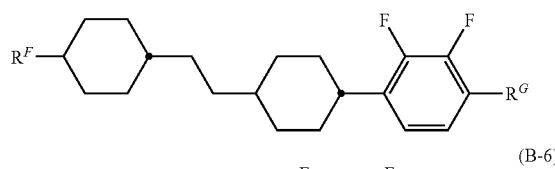
(B-5)

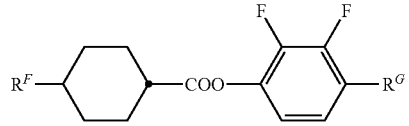
(B-6)

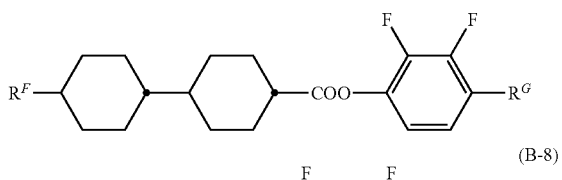
(B-7)

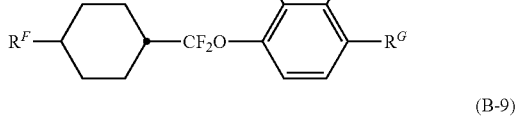
(B-8)

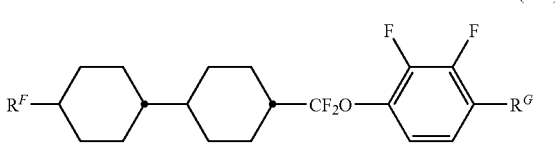
(B-9)

In the above formulas, $R^F$ represents a linear alkyl group having 1 to 7 carbon atoms; and $R^G$ represents a linear alkyl group having 1 to 5 carbon atoms, or a linear alkoxyl group having 1 to 4 carbon atoms.

Moreover, in the liquid crystal composition of the present invention, it may contain one or more kinds of compounds represented by the general formula (C) to the general formula (G).

[Chemical formula 23]

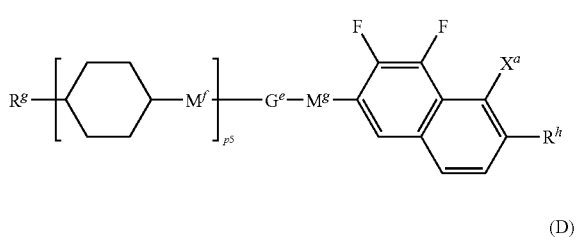
(C)

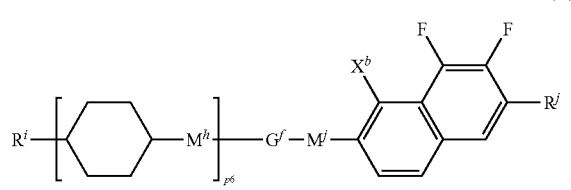
(D)

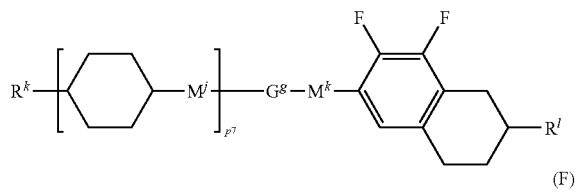
(E)

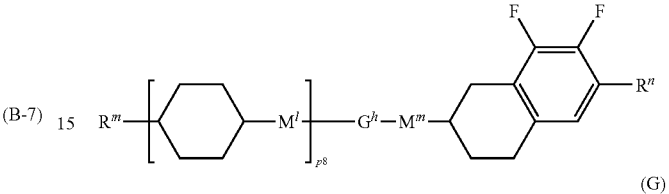
(F)

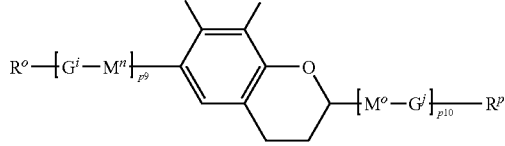
(G)

(In the formulas, $R^g$, $R^i$, $R^k$, and $R^m$ represent a linear alkyl group having 1 to 7 carbon atoms; $R^h$, $R^j$, and $R^n$ represent a linear alkyl group, an alkoxyl group, or an alkenyloxy group having 1 to 7 carbon atoms; $R^l$ represents a linear alkyl group having 1 to 7 carbon atoms; $R^o$ represents a linear alkyl group, an alkoxyl group having 1 to 7 carbon atoms, or a linear alkenyl group, alkenyloxy group having 2 to 7 carbon atoms; $R^p$ represents a linear alkyl group having 1 to 7 carbon atoms, or a linear alkenyl group having 2 to 7 carbon atoms; $X^a$ and $X^b$ represent a hydrogen atom or a fluorine atom; each p5, p6, p7, and p8 represents independently 0 or 1; each p9 and p10 represents independently 0, 1 or 2; the sum of p9 and p10 is 1 or 2; each $M^f$ and $M^g$, $M^h$ and $M^i$, $M^j$ and $M^k$, $M^l$, $M^m$, and $M^n$ represents independently a single bond, —$CH_2CH_2$—, —$OCH_2$—, —$CH_2O$—, —$OCF_2$—, —$CF_2O$—, or —COO—; $M^o$ represents a single bond or —$CH_2CH_2$—; each $G^e$, $G^f$, $G^g$, $G^h$, $G^i$, and $G^j$ represents independently a trans-1,4-cyclohexylene group or -1,4-phenylene group which may be replaced with 1 or 2 fluorine atoms; and in the case when a choice of $G^i$, $G^j$, $M^n$ and $M^o$ are, they may be same, or may be different.)

In the general formula (C) to the general formula (G), it is preferable that $R^g$, $R^i$, $R^k$, $R^m$, and $R^p$ is a linear alkyl group having 2 to 7 carbon atoms. It is preferable that $R^h$, $R^j$, $R^n$, and $R^o$ is a linear alkyl group, a linear alkoxyl group having 1 to 5 carbon atoms. It is preferable that $R^l$ is a linear alkyl group having 1 to 3 carbon atoms. Each $M^f$ and $M^g$, $M^h$ and $M^i$, $M^j$ and $M^k$, $M^l$ and $M^m$ represents independently a single bond, —$CH_2CH_2$—, —$OCH_2$—, —$CH_2O$—, —$OCF_2$—, —$CF_2O$—, or —COO—; it is preferable that one is a single bond, and the other is a single bond, —$CH_2CH_2$—, or —COO—. It is preferable that $M^n$ is a single bond, —$CH_2CH_2$—, —$CH_2O$—, or —$CF_2O$—.

Embodiments

Hereinafter is a further description of the present invention with reference to embodiments. However, the present invention is not to be limited to these embodiments.

Further, the measurement of phase transition temperature was performed with a polarizing microscope equipped with a hot stage and together with a differential scanning calorimeter (DSC). Also, the structure of the compounds was confirmed by nuclear magnetic resonance spectrum (NMR), infrared resonance spectrum (IR), mass spectrum (MS), and the like.

EXAMPLE 1

Synthesis of 7-butoxy-3-[2-(trans-4-propylcyclohexyl)ethyl]-1,2-difluoro-8-trifluoromethylnaphthalene (I-1)

[Chemical formula 24]

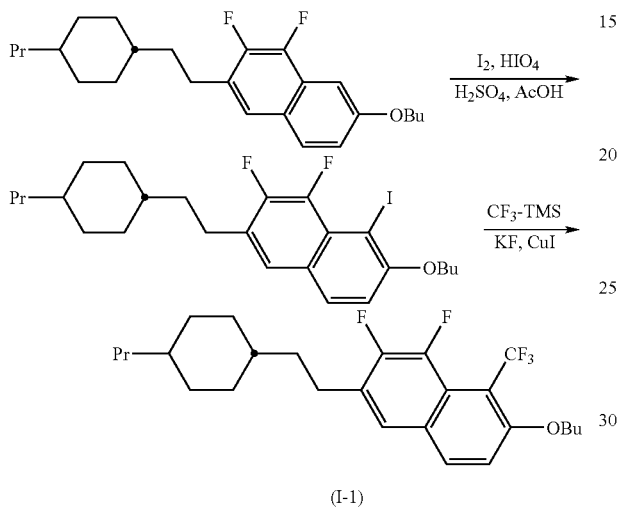

(I-1)

EXAMPLE 1-1

7-butoxy-3-[2-(trans-4-propylcyclohexyl)ethyl]-1,2-difluoro-8-iodonaphthalene (The following is performed in a draft chamber.) A mixture of concentrated sulfuric acid (1.5 ml), water (10 ml), and glacial acetic acid (50 ml) was dropped for about 10 minutes into a suspension of 7-butoxy-3-[2-(trans-4-propylcyclohexyl)ethyl]-1,2-difluoronaphthalene(21.4 g, 0.053 mol), periodic acid dihydrate (2.6 g, 0.011 mol), and iodine (5.4 g, 0.021 mol) in glacial acetic acid (100 ml) with vigorously stirring. After stirring at 60° C. for 4 hours, the reaction liquid was cooled, poured into water, and the reaction was terminated. The precipitated solid was dissolved with toluene, the organic layer was separated, and was extracted with toluene from the aqueous layer. After collecting organic layers, it was rinsed, in order, with 10% sodium thiosulfate aqueous solution, with saturated sodium hydrogen carbonate aqueous solution, and with saturated brine, and was dried with anhydrous sodium sulfate. A light yellow solid (21.4 g) was obtained by removing the solvent under reduced pressure and by recrystallizing the obtained orange solid (from acetone). (Yield 73.9%)

EXAMPLE 1-2

7-butoxy-3-[2-(trans-4-propylcyclohexyl) ethyl]-1,2-difluoro-8-trifluoromethylnaphthalene (I-1)

(The following is performed in a draft chamber.) (Trifluoromethyl) trifluoromethane (9.1 ml, 0.062 mol) was added into a suspension of 7-butoxy-3-[2-(trans-4-propylcyclohexyl)ethyl]-1,2-difluoro-8-iodonaphthalene (21.4 g, 0.042 mol), potassium fluoride (3.2 g, 0.055 mol), and copper(I) iodide (11.6 g, 0.061 mol) in an anhydrous N,N-dimethylformamide (110 ml) with vigorously stirring. After carrying out stirring with heating at 70° C. for 24 hours, the reaction liquid was cooled, poured into water, and the reaction was terminated. After filtering copper salt using Celite, the salt was rinsed with ethyl acetate, the filtrates were mixed, the organic layer was separated, and it was extracted with ethyl acetate from the aqueous layer. After collecting organic layers, it was rinsed, in order, with 10% sodium thiosulfate aqueous solution, with saturated sodium hydrocarbon aqueous solution, and with saturated brine, and it was dried with anhydrous sodium sulfate. Colorless needle crystals (9.9 g) were obtained by removing the solvent under reduced pressure, by purifying the obtained orange solid using a column chromatography (silica gel/hexane+dichloromethane), and by recrystallizing (from ethanol with methanol). (Yield 51.2%)

1H-NMR(400 MHz, CDCl$_3$) δ(ppm) 0.87 (t, 3H), 0.99 (t, 3H) 0.82-1.04 (m, 2H), 1.12-1.37 (m, 6H), 1.48-1.61 (m, 4H), 1.72-1.88 (m, 6H), 2.79 (t, 2H), 4.15 (t, 2H), 7.23 (d, J=9.2 Hz, 1H), 7.36 (dm, J=6.0 Hz, 1H), 7.82 (d, J=8.8 Hz, 1H)

Phase transition temperature (° C.) Cr 58 N 62.5 Iso

EXAMPLE 2

Preparation (1) of a Liquid Crystal Composition

A host liquid crystal composition (H) comprising the following constitution was prepared.

[Chemical formula 25]

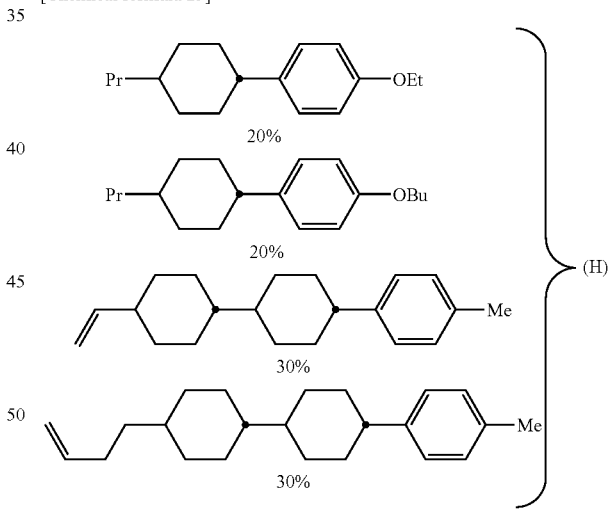

Here, the values of physical properties of (H) are as follows.

| | |
|---|---|
| Upper limit temperature of the Nematic phase($T_{N-I}$): | 103.2° C. |
| Dielectric anisotropy (Δε): | 0.03 |
| Birefringence (Δn): | 0.099 |

The liquid crystal composition (M-1) comprising 80% of the host liquid crystal (H) and 20% (I-1) obtained in the example 1 was prepared. The values of the physical properties of the composition are as follows.

| | |
|---|---|
| Upper limit temperature of the Nematic phase($T_{N\text{-}I}$): | 93.6° C. |
| Dielectric anisotropy (Δε): | −2.09 |
| Birefringence (Δn): | 0.103 |

The dielectric anisotropy (Δ∈) of the liquid crystal composition (M-1) containing the compound (I-1) of the present invention decreased greatly and became a negative value compared to the host liquid crystal (H). It is understood from the result that the dielectric anisotropy of the compound (I-1) of the present invention is negative and its absolute value is very large.

Furthermore, measuring the voltage holding ratio of (M-1) at 80° C., a high value of 98% or more was shown to the voltage holding ratio of the host liquid crystal composite (H). It is understood from the result that the compound (I-1) of the present invention can be sufficiently used as a liquid crystal display material also in respect of stability.

COMPARATIVE EXAMPLE 1

Preparation (2) of a Liquid Crystal Composition

A liquid crystal composition (M-2) comprising the host liquid crystal (H) prepared in the example 1 and 10% of a compound (J-1)

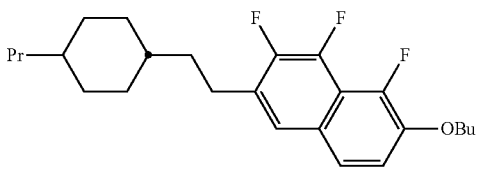

(J-1)

which had comparatively similar structure to the compound (I-1) but in which a trifluoromethyl group was replaced with a fluorine atom was prepared. The values of physical properties of the composition are as follows.

| | |
|---|---|
| Upper limit temperature of the Nematic phase($T_{N\text{-}I}$): | 95.4° C. |
| Dielectric anisotropy (Δε): | −1.33 |
| Birefringence (Δn): | 0.106 |

It is understood from the result that the absolute value of the dielectric anisotropy of the liquid crystal composition (M-2) containing the compound (J-1) has smaller absolute value than the value of (M-1) described in the example 1.

EXAMPLE 3

Preparation (3) of a Liquid Crystal Composition

A liquid crystal composition (M-3) comprising the following constitution was prepared.

[Chemical formula 27]

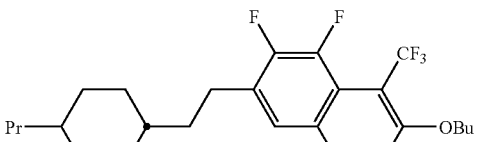

20%

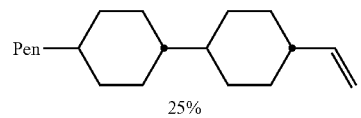

25%

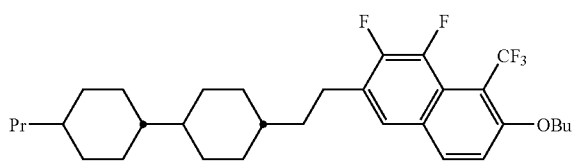

10%

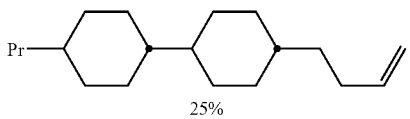

25%

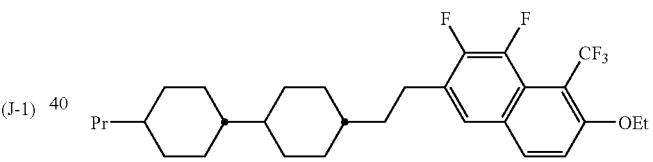

10%

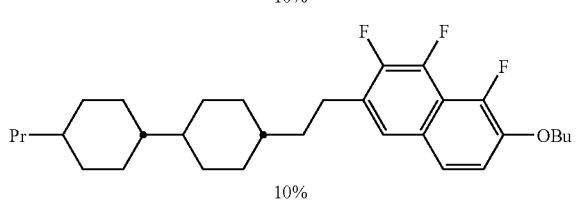

10%

The values of physical properties of (M-3) were as follows.

| | |
|---|---|
| Upper limit temperature of the Nematic phase($T_{N\text{-}I}$): | 100.1° C. |
| Dielectric anisotropy (Δε): | −4.06 |
| Birefringence (Δn): | 0.094 |

As a result of measuring the voltage holding ratio using the composition prepared here, a high value of 98% at 80° C. was shown, and a liquid crystal display apparatus of excellent displaying characteristics could be manufactured.

EXAMPLE 4

Preparation (4) of a Liquid Crystal Composition

A liquid crystal composition (M-4) comprising the following constitution was prepared.

[Chemical formula 28]

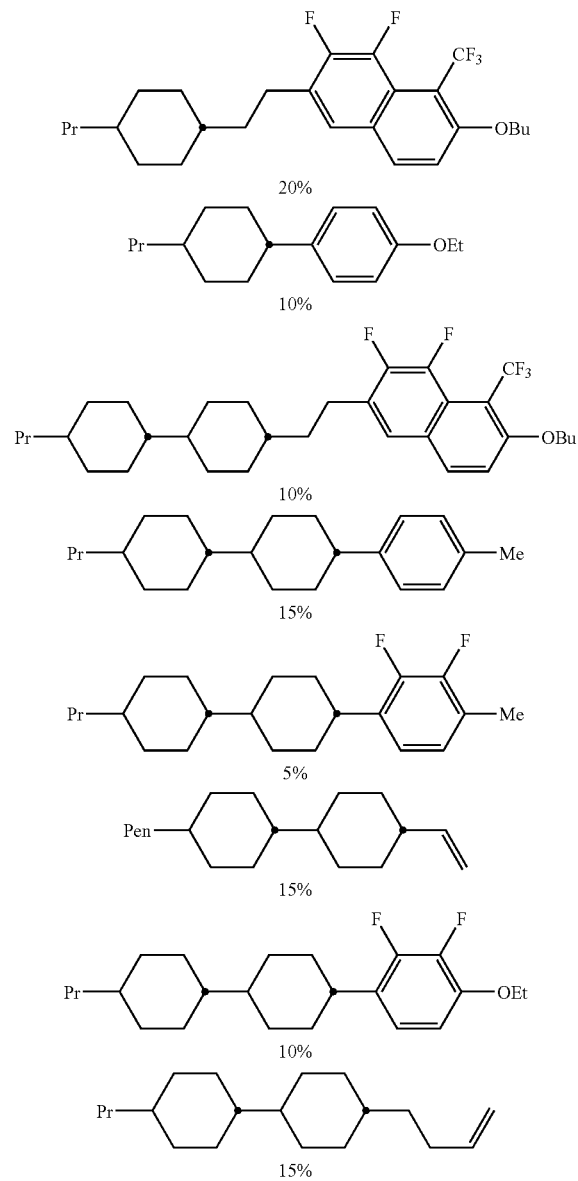

The values of physical properties of (M-4) were as follows.

| | |
|---|---:|
| Upper limit temperature of the Nematic phase($T_{N-I}$): | 100.0° C. |
| Dielectric anisotropy (Δε): | −3.59 |
| Birefringence (Δn): | 0.094 |

As a result of measuring the voltage holding ratio using the composition prepared here, a high value of 98% at 80° C. was shown, and a liquid crystal display apparatus of excellent displaying characteristics could be manufactured.

EXAMPLE 5

Synthesis of 7-butoxy-1,2-difluoro-3-(trans-4-propylcyclohexyl)methoxy-8-trifluoromethylnaphthalene (I-2)

[Chemical formula 29]

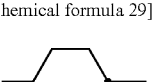

7-butoxy-1,2-difluoro-3-[2-(trans-4-propylcyclohexyl)methoxy]-8-iodonaphthalene was obtained using 7-butoxy-1,2-difluoro-3-(trans-4-propylcyclohexyl)methoxy naphthalene, replacing with 7-butoxy-1,2-difluoro-3-[2-(trans-4-propylcyclohexyl)ethyl]-naphthalene of the example 1-1.

7-butoxy-1,2-difluoro-3-(trans-4-propylcyclohexyl)methoxy-8-trifluoromethylnaphthalene was obtained using the above-mentioned 7-butoxy-1,2-difluoro-3-[2-(trans-4-propylcyclohexyl)methoxy]-8-iodonaphthalene, replacing with 7-butoxy-1,2-difluoro-3-[2-(trans-4-propylcyclohexyl)ethyl]-8-iodonaphthalene of the example 1-2.

$^1$H-NMR (400 MHz, CDCl$_3$) δ 0.87-1.96 (m, 24H), 3.91 (d, J=4.8 Hz, 2H), 4.13 (t, J=4.9 Hz, 2H), 6.97 (d, J=4.2 Hz, 1H), 7.22-7.26 (m, 1H), 7.77 (d, J=7.2 Hz, 1H) MS m/z 458 (M$^+$)

Phase transition temperature (° C.) Cr 96 (SmB 70) I

EXAMPLE 6

Synthesis of 7-butoxy-1,2-difluoro-3-(trans,trans-4-propylbicyclohexyl-4-yl)methoxy-8-trifluoromethyl-naphthalene (I-3)

[Chemical formula 30]

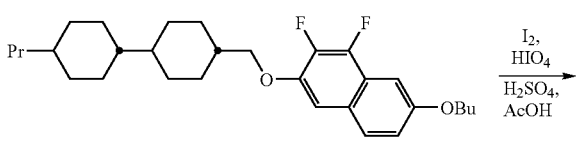

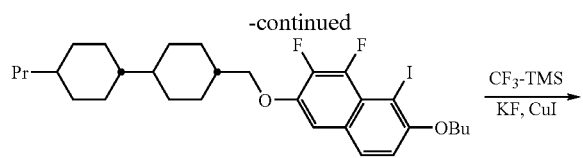

(I-3)

7-butoxy-1,2-difluoro-3-(trans,trans,4-propylbicyclo-hexyl-4-yl)methoxy-8-iodonaphthalene was obtained using 7-butoxy-1,2-difluoro-3-(trans,trans,4-propylbicyclohexyl-4-yl)methoxy naphthalene, replacing with 7-butoxy-1,2-difluoro-3-[2-(trans-4-propylcyclohexyl)ethyl]naphthalene of the example 1-1.

7-butoxy-1,2-difluoro-3-(trans,trans-4-propylbicyclohexyl-yl)methoxy-8-trifluoromethylnaphthalene was obtained using the above-mentioned 7-butoxy-1,2-difluoro-3-(trans,trans-4-propylbicyclohexyl-4-yl)methoxy-8-iodonaphthalene, replacing 7-butoxy-1,2-difluoro-3-[2-(trans-4-propylcyclohexyl)ethyl]-8-iodonaphthalene of the example 1-2.

$^1$H-NMR (400 MHz, CDCl$_3$) δ 0.83-1.86 (m, 34H), 3.90 (d, J=5.1 Hz, 2H), 4.13 (t, J=4.8 Hz, 2H), 6.96 (dd, J=5.7, 1.5 Hz, 1H), 7.22-7.24 (m, 1H), 7.77 (d, J=6.6 Hz, 1H)

MS m/z 540 (M$^+$)

Phase transition temperature (° C.) Cr 117 SmA 137 N 202 I

EXAMPLE 7

Synthesis of 1,2-difluoro-7-pentyl-3-(trans,trans-4-propylbicyclohexyl-4-yl)methoxy-8-trifluoromethyl-naphthalene (I-4)

1,2-difluoro-7-pentyl-3-(trans,trans-4-propylbicyclohexyl-4-yl) methoxy-8-iodonaphthalene was obtained using 1,2-difluoro-7-pentyl-3-(trans,trans-4-propylbicyclohexyl-4-yl)methoxy naphthalene, replacing with 7-butoxy-3-[2-(trans-4-propylcyclohexyl)ethyl]-1,2-difluoronaphthalene of the example 1-1.

1,2-difluoro-7-pentyl-3-(trans,trans-4-propylbicyclohexyl-4-yl)methoxy-8-trifluoromethylnaphthalene was obtained using the above-mentioned 1,2-difluoro-7-pentyl-3-(trans,trans-4-propylbicyclohexyl-4-yl)methoxy-8-iodonaphthalene, replacing with 7-butoxy-3-[2-(trans-4-propylcyclohexyl)ethyl]-1,2-difluoro-8-iodonaphthalene of the experiment 1-2.

$^1$H-NMR (400 MHz, CDCl$_3$) δ 0.84-1.97 (m, 36H), 2.90-2.95 (m, 2H), 3.92 (d, J=4.8 Hz, 2H), 6.99 (dd, J=6.0, 1.2 Hz, 1H), 7.26-7.28 (m, 1H), 7.71 (d, J=6.6 Hz, 1H)

MS m/z 538 (M$^+$)

Phase transition temperature (° C.) Cr 124 N 166 I

EXAMPLE 8

Preparation (6) of a Liquid Crystal Composition

A liquid crystal composition (M-2) comprising the host liquid crystal (H) prepared in the example 2 and 10% of the compound (I-2) was prepared. The values of physical properties of the composition are as follows.

[Chemical formula 32]

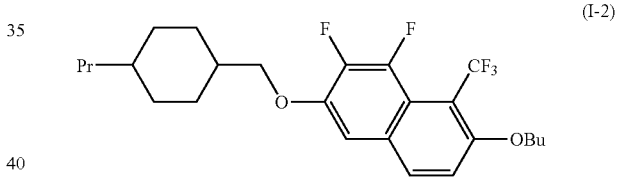

(I-2)

[Chemical formula 31]

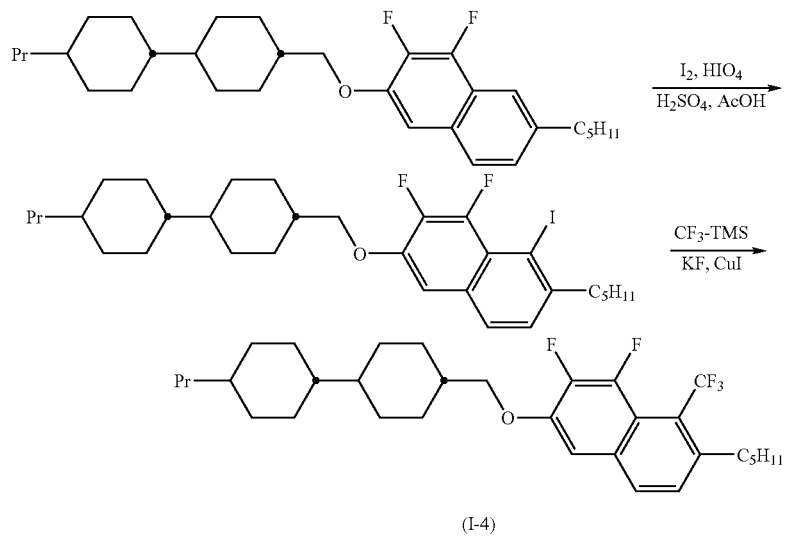

(I-4)

| | |
|---|---|
| Upper limit temperature of the Nematic phase($T_{N-I}$): | 99.3° C. |
| Dielectric anisotropy (Δε): | −1.36 |
| Birefringence (Δn): | 0.101 |

The dielectric anisotropy (Δε) of the liquid crystal composition (M-2) containing the compound (I-2) of the present invention decreased greatly and became a negative value compared to the host liquid crystal (H). It is understood from the result that the compound (I-2) of the present invention has negative dielectric anisotropy, and its absolute value is extremely large.

Also, as a result of measuring the voltage holding ratio of (M-2) at 80° C., a high value of 98% or more to the voltage holding ratio of the host liquid crystal composition (H) was shown. It is understood from the result that the compound (I-2) of the present invention can be sufficiently used as a liquid crystal display material also in respect of stability.

EXAMPLE 9

Preparation (6) of a liquid crystal Composition

A liquid crystal composition (M-3) comprising the host liquid crystal (H) prepared in the example 2 and 10% of the compound (1-3) was prepared.

[Chemical formula 33]

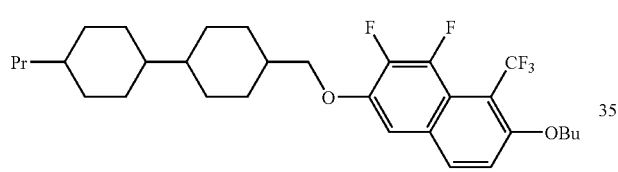

(I-3)

The values of physical properties of the composition are as follows.

| | |
|---|---|
| Upper limit temperature of the Nematic phase($T_{N-I}$): | 111.0° C. |
| Dielectric anisotropy (Δε): | −1.23 |
| Birefringence (Δn): | 0.102 |

The dielectric anisotropy (Δε) of the liquid crystal composition (M-2) containing the compound (I-3) of the present invention decreased greatly and became a negative value compared to the host liquid crystal (H). It is understood from the result that the compound (I-3) of the present invention has negative dielectric anisotropy, and the absolute value is extremely large.

Also, as a result of measuring the voltage holding ratio of (M-3) at 80° C., a high value of 98% or more to the voltage holding ratio of the host liquid crystal composition (H) was shown. It is understood from the result that the compound (I-3) of the present invention can be sufficiently used as a liquid crystal display material also in respect of stability.

EXAMPLE 10

Preparation (7) of a Liquid Crystal Composition

A liquid crystal composition (M-4) comprising the host liquid crystal (H) prepared in the example 2 and 10% of the compound (I-4) was prepared.

[Chemical formula 34]

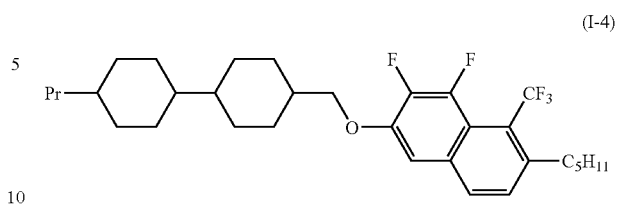

(I-4)

The values of physical properties of the composition are as follows.

| | |
|---|---|
| Upper limit temperature of the Nematic phase($T_{N-I}$): | 107.8° C. |
| Dielectric anisotropy (Δε): | −0.81 |
| Birefringence (Δn): | 0.102 |

The dielectric anisotropy (Δε) of the liquid crystal composition (M-4) containing the compound (I-4) of the present invention, compared to the host liquid crystal (H), decreased greatly and became a negative value. It is understood from the result that the compound of the present invention (I-4) has negative dielectric anisotropy, and the absolute value is extremely large.

Also, as a result of measuring the voltage holding ratio of (M-4) at 80° C., a high value of 98% or more to the voltage holding ratio of the host liquid crystal composition (H) was shown. It is understood from the result that the compound (I-4) of the present invention can be sufficiently used as a liquid crystal display material also in respect of stability.

The invention claimed is:

1. A 1-(trifluoromethyl)naphthalene derivative represented by the general formula (I)

[Chemical Formula 1]

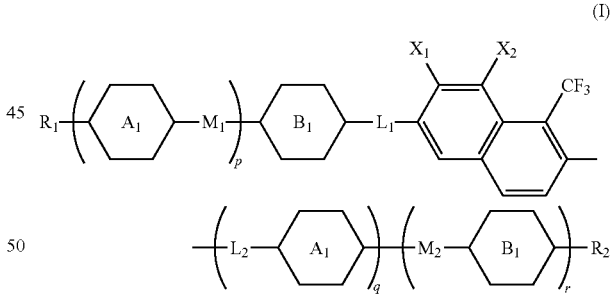

(I)

wherein, in the formula, each $R_1$ and $R_2$ represents independently an alkyl group having 1 to 12 carbon numbers, an alkenyl group having 2 to 12 carbon numbers, an alkoxyl group having 1 to 12 carbon numbers, or an alkenyloxy group having 2 to 12 carbon numbers;

each one or more hydrogen atoms may be independently replaced with a fluorine atom, and each -$CH_2$- group may be independently replaced with —O—, —S—, —CO—, —COO—, —OCO—, or —OCOO—;

each $A_1$, $A_2$, $B_1$, and $B_2$ represents independently a trans-1,4-cyclohexylene group or a 1-4-phenylene group which may be replaced with one or more fluorine atoms;

each $L_1$, $L_2$, $M_1$, and $M_2$ represents independently a single bond, —$CH_2CH_2$—, —CH=CH—, —C≡C—, —OCH$_2$—, —CH$_2$O—, —OCF$_2$—, —CF$_2$O—, —CF$_2$CF$_2$—, —CF=CF—, —OCO—, —COO—, —CH(CH$_3$)CH$_2$—, —CH$_2$CH(CH$_3$)—, —CH(CH$_3$)CH(CH$_3$)—, —OCH(CH$_3$)—, —CH(CH$_3$)O—, —(CH$_2$)$_4$—, —(CH$_2$)$_3$O—, —O(CH$_2$)$_3$—, —COS—, or —SCO—;

each X$_1$ and X$_2$ represents independently a hydrogen atom or a fluorine atom; and each p, q, r, and s represents independently 0 or 1.

2. The compound in the general formula (I) according to claim 1, wherein each R$_1$ and R$_2$ represents independently an alkyl group having 1 to 8 carbon numbers, an alkenyl group having 2 to 8 carbon numbers, an alkoxyl group having 1 to 7 carbon numbers, or an alkenyloxy group having 2 to 7 carbon numbers, in which each one or more hydrogen atoms may be independently replaced with a fluorine atom.

3. The compound in the general formula (1) according to claim 1, wherein each L$_1$, L$_2$, M$_1$, and M$_2$ represents independently a single bond, —CH$_2$CH$_2$—, —OCH$_2$—, —CH$_2$O—, —OCF$_2$—, —CF$_2$O—, or —CF$_2$CF$_2$—.

4. The compound in the general formula (I) according to claim 1, wherein X$_1$ and X$_2$ represent a fluorine atom.

5. The compound in the general formula (I) according to claim 1, wherein a sum of p, q, r and s represents an integer of 1 or more and 3 or less.

6. The compound in the general formula (I) according to claim 1, wherein each L$_1$, L$_2$, M$_1$, and M$_2$ represents independently a single bond or —CH$_2$CH$_2$—.

7. The compound in the general formula (I) according to claim 1, wherein a sum of p, q, r and s represents 1 or 2.

8. A liquid crystal composition which contains at least one of the compounds represented by the general formula (I) according to claim 1.

9. A liquid crystal device which comprises the liquid crystal composition according to claim 8 as a constituent element.

10. A liquid crystal composition which contains at least one of the compounds represented by the general formula (1) according to claim 2.

11. A liquid crystal composition which contains at least one of the compounds represented by the general formula (I) according to claim 3.

12. A liquid crystal composition which contains at least one of the compounds represented by the general formula (I) according to claim 4.

13. A liquid crystal composition which contains at least one of the compounds represented by the general formula (I) according to claim 5.

14. A liquid crystal composition which contains at least one of the compounds represented by the general formula (I) according to claim 6.

15. A liquid crystal composition which contains at least one of the compounds represented by the general formula (I) according to claim 7.

16. A liquid crystal device which comprises the liquid crystal composition according to claim 10 as a constituent element.

17. A liquid crystal device which comprises the liquid crystal composition according to claim 11 as a constituent element.

18. A liquid crystal device which comprises the liquid crystal composition according to claim 12 as a constituent element.

19. A liquid crystal device which comprises the liquid crystal composition according to claim 13 as a constituent element.

20. A liquid crystal device which comprises the liquid crystal composition according to claim 14 as a constituent element.

\* \* \* \* \*